United States Patent
Klieman et al.

(10) Patent No.: US 8,407,064 B1
(45) Date of Patent: Mar. 26, 2013

(54) METHOD AND SYSTEM FOR HEALTHCARE BENEFIT PLAN SELECTION

(75) Inventors: Michael S. Klieman, Belmont, CA (US); Michael A. Battaglia, Louisville, KY (US); Muhammet Serdar Akin, Santa Clara, CA (US)

(73) Assignee: Intuit Inc., Mountain View, CA (US)

( * ) Notice: Subject to any disclaimer, the term of this patent is extended or adjusted under 35 U.S.C. 154(b) by 1241 days.

(21) Appl. No.: 11/754,816

(22) Filed: May 29, 2007

(51) Int. Cl.
*G06Q 10/00* (2012.01)
(52) U.S. Cl. ..................................... 705/2; 705/3; 705/4
(58) Field of Classification Search ................... 705/2, 4
See application file for complete search history.

(56) References Cited

U.S. PATENT DOCUMENTS

| | | | |
|---|---|---|---|
| 7,444,291 B1 * | 10/2008 | Prasad et al. ....................... 705/2 |
| 7,693,728 B2 * | 4/2010 | Underwood et al. .............. 705/2 |
| 7,702,527 B1 | 4/2010 | Kron et al. |
| 2002/0147617 A1 * | 10/2002 | Schoenbaum et al. ............ 705/4 |
| 2005/0055251 A1 | 3/2005 | Ashley et al. |
| 2005/0251428 A1 * | 11/2005 | Dust et al. .......................... 705/4 |
| 2007/0027727 A1 * | 2/2007 | Cochrane .......................... 705/4 |
| 2007/0233515 A1 * | 10/2007 | Mehus et al. ...................... 705/2 |
| 2008/0010086 A1 | 1/2008 | Skelly et al. |

OTHER PUBLICATIONS

Klieman et al., "Method and System for Optimizing Healthcare Benefits for Early Retirement", U.S. Appl. No. 12/019,303, filed Jan. 24, 2008.
Elwell et al., "Method and System for Healthcare Plan Selection", U.S. Appl. No. 12/844,096, filed Jul. 27, 2010.
OPM.GOV, "Insurance Quick Guide", 2005, 7 pages.

* cited by examiner

*Primary Examiner* — Valerie Lubin
(74) *Attorney, Agent, or Firm* — McKay and Hodgson, LLP; Philip McKay; Sean P. Lewis (57) ABSTRACT

A method and system for healthcare benefit plan selection determines a healthcare consumer's projected/predicted healthcare service utilization for a defined timeframe using a personalized healthcare service utilization model created based on: general/demographic data associated with the healthcare consumer; the healthcare consumer's historical healthcare service utilization; and the healthcare consumer's personal health profile data. Data associated with the rules governing the operation and use of two or more candidate healthcare benefit plans is also obtained. The operation and rules of use are then applied to healthcare consumer's projected healthcare service utilization for the defined timeframe to create expected healthcare consumer experience model data under each of two or more candidate healthcare benefit plans. In one embodiment, comparison data and/or a plan recommendation is then provided to the healthcare consumer.

19 Claims, 2 Drawing Sheets

METHOD AND SYSTEM FOR HEALTHCARE BENEFIT PLAN SELECTION

BACKGROUND

Most healthcare consumers are keenly aware that healthcare costs have risen dramatically over the past decade. As the cost the healthcare itself has gone up, so has the cost of health insurance and healthcare benefit plans. Indeed, over the past decade, a twenty percent or greater increase in health insurance premiums in a single year has been commonplace. All indications are that this trend will continue. As a result, many employers and/or organizations have had to pass on to their employees/members a progressively greater share of the financial burden of healthcare benefit plans.

To help alleviate some of this financial burden, or at least give the employees/members more control over their expenditures, many employers and/or organizations now offer multiple healthcare benefit plans, often administered by multiple healthcare benefit plan providers. For example, an employer may offer employees a choice of one or more medical insurance plans, dental insurance plans, and vision services plans, any of which may be considered a health insurance plan and/or a healthcare benefit plan. In another example, a healthcare consumer may have the opportunity to purchase medical insurance through an industry organization, fraternal organization, labor union, alumni organization, or any other organization to which he or she belongs.

Each of these health care benefit plans has different plan characteristics. These plan characteristics include, but are not limited to: the conditions, services, treatments, and medications covered by the plans; the individual healthcare providers, provider groups, and healthcare facilities participating in the plans; the premiums paid by the employer/organization and/or the employees/members for employees/members and their eligible dependents; the specific deductibles, co-payments, out-of-pocket yearly maximum expenses, lifetime maximum expenses, and other financial characteristics; and the portability of the healthcare benefit plan and/or health insurance plan, i.e., is the plan only available while the consumer is an employee/member. In addition, different types of health insurance plans may be offered as, or as part of, a healthcare benefit plan, such as plans managed by a Health Maintenance Organization (HMOs), plans managed by a Preferred Provider Organization (PPOs), or High Deductible Health Plans (HDHPs).

In addition, in order to help employees further offset increased healthcare costs, many employers now offer healthcare expense account programs that are typically used in addition to, and often in conjunction with, traditional health insurance. Herein, healthcare expense account programs are defined as programs which provide an employee/healthcare consumer and/or employee's/healthcare consumer's dependents a designated healthcare expense account that is assigned to the employee/healthcare consumer and is used to reimburse the employee/healthcare consumer for defined eligible healthcare expenses incurred by the employee/healthcare consumer and/or the employee's/healthcare consumer's dependents. Typically, healthcare expense account programs are tax-advantaged accounts whereby the employee/healthcare consumer can use pre-tax funds to pay eligible healthcare expenses incurred by the employee/healthcare consumer and/or the employee's/healthcare consumer's dependents. Examples of currently available healthcare expense account programs include, but are not limited to: flexible spending accounts (FSAs); healthcare reimbursement arrangements (HRAs); and healthcare spending accounts (HSAs).

In addition, due, in part, to the increased cost of employer/organization sponsored programs and/or the desire to obtain a healthcare benefit plan that is not dependent on an employer, employment status, and/or an organization, many healthcare consumers desire information about self-sponsored healthcare benefit plans and want to consider, and/or enroll in, these programs as an alternative and/or supplement to any employer/organization sponsored programs.

As a result of the situation described above, healthcare consumers must often make multiple healthcare benefit plan decisions, including, but not limited to, which healthcare benefit plan to enroll in. However, in order to make an intelligent decision, the healthcare consumer is faced with a seemly overwhelming amount of data regarding the plan characteristics discussed above.

Given the number of variables and considerations associated with choosing a healthcare benefit plan, it is not surprising that many healthcare consumers feel overwhelmed by the process. As a result, many healthcare consumers do not feel they have the time or energy to gather and analyze all the relevant characteristic data for each plan. Consequently, these healthcare consumers often make this very important, and potentially life changing, decision in a somewhat uninformed and ad-hoc manner. On the other hand, those that do wade through all the data and various plan characteristics are often significantly inconvenienced by the process and, in some cases, are left feeling even more confused as a result of their considerable effort.

Currently, some methods and processes for helping healthcare consumer's choose a healthcare plan are available. However, these methods and processes typically provide highly generalized benchmark data and/or, at best, analysis based almost entirely on historical usage data. Consequently, these currently available methods and processes for helping a healthcare consumer choose a healthcare plan do not take into account predictable future health conditions in any meaningful and/or personalized way.

SUMMARY

In accordance with one embodiment, a method and system for healthcare benefit plan selection includes a process for healthcare benefit plan selection whereby, in one embodiment, the healthcare consumer's projected healthcare service utilization for a defined timeframe is determined using a personalized healthcare service utilization model. In one embodiment, the personalized healthcare service utilization model is created using: general/demographic data associated with the healthcare consumer; the healthcare consumer's historical healthcare service utilization, including past medical claims data; and the healthcare consumer's personal health profile data. In one embodiment, data associated with the rules governing the operation and use of two or more candidate healthcare benefit plans available to the healthcare consumer is also obtained. In one embodiment, the rules governing the operation and use of the two or more candidate healthcare benefit plans are then applied to healthcare consumer's projected healthcare service utilization data for the defined timeframe to create expected healthcare consumer experience data under each of two or more candidate healthcare benefit plans. In one embodiment, the expected healthcare consumer experience data are then compared. In one embodiment, comparison data and/or a plan recommendation is then provided to the healthcare consumer.

Herein, the terms "healthcare consumer", "user", and/or "consumer" are used to denote a person who is entitled to benefits, reimbursement, and/or service under a healthcare benefit plan. Herein, the a healthcare consumer can be a primary and/or responsible party under a healthcare benefit plan and/or any dependents of the primary and/or responsible party and/or any other parties entitled to benefits and/or service under a healthcare benefit plan.

In one embodiment, a timeframe is defined for the analysis of the process for healthcare benefit plan selection. In various embodiments the defined timeframe can be any period desired, such as, but not limited to, months, years, decades, working lifetime, and/or lifetime. In one embodiment, the defined timeframe is the time between open enrollment periods in an employer/organization sponsored healthcare benefit plan and/or a defined healthcare benefit plan year.

In one embodiment, the healthcare consumer's general background data is obtained. In one embodiment, the general background data includes general/demographic data such as, but not limited to: data manually entered by the healthcare consumer; age; sex; occupation; residence; etc. and the recommended and/or average utilization of the average person of the healthcare consumer's background over the defined timeframe.

In one embodiment, the healthcare consumer's historical healthcare utilization data is also obtained. In one embodiment, the healthcare consumer's historical healthcare utilization data includes, but is not limited to: data manually entered by the healthcare consumer; data representing the healthcare consumer's actual historical utilization of the healthcare services; data representing the healthcare consumer's past medical claims; data indicating whether or not the healthcare consumer actually takes advantage of regularly scheduled check ups and/or other preventative measures; whether the healthcare consumer follows and/or stays on any recommended routines, programs and/or medications; the healthcare consumer's family medical history; and/or the healthcare consumer's overall usage and historical attitude towards healthcare in general.

In one embodiment, the healthcare consumer's personal health profile data is also obtained. In one embodiment, the healthcare consumer's personal health profile data includes, but is not limited to: data manually entered by the healthcare consumer; clinical data regarding existing disease, diagnoses, and/or treatment programs; the likely result of a diagnosed healthcare consumer condition based on the general disposition of the healthcare consumer to making use of available healthcare services and/or following medical advice; trends/patterns in the healthcare consumer's specific clinical medical history and/or lab results; activities the healthcare consumer takes part in; the healthcare consumer's general activity level; and/or any other healthcare consumer health profile data that is indicative of health risks and/or pre-dispositions to disease and/or injury specific to the healthcare consumer.

In one embodiment, the healthcare consumer's general background data, the healthcare consumer's historical healthcare utilization data; the healthcare consumer's personal health profile data; and any other data desired and/or obtained is used to create a personalized projected healthcare service utilization model for the healthcare consumer that predicts the healthcare consumer's projected healthcare service utilization for the defined period.

In one embodiment, once the personalized projected healthcare service utilization model for the healthcare consumer provides predicted healthcare service utilization data, the process for healthcare benefit plan selection disclosed herein obtains healthcare benefit plan operation data indicating the specific rules governing the operation and use of two or more candidate healthcare benefit plans available to the healthcare consumer. In one embodiment, the healthcare benefit plan operation data includes, but is not limited to: a description and/or listing of the benefits offered under each plan; a description and/or listing of the financial obligation of the healthcare consumer under each plan, i.e., deductibles, co-payments, and healthcare consumer responsibility for different types of procedures, under each plan; the number of providers and the area of the provider network in each plan; how the healthcare expense account programs work within each plan; and/or data representing any other criteria and/or considerations associated with each plan as desired/defined by the healthcare consumer and/or the provider of the process for healthcare benefit plan selection.

In one embodiment, the healthcare consumer's portion of the cost of the projected healthcare service utilization for the defined timeframe, i.e., the healthcare consumer's "out-of-pocket" cost for the projected healthcare service utilization for the defined timeframe, is then calculated/predicted for each of the two or more candidate healthcare benefit plans.

In one embodiment, the calculated out-of-pocket cost of the healthcare consumer's projected healthcare service utilization for the defined timeframe under each of the two or more candidate healthcare benefit plans is then compared and the comparison data is provided to the healthcare consumer along with, in one embodiment, a healthcare benefit plan recommendation.

In one embodiment, data representing various other characteristics of each of the two or more candidate healthcare benefit plans available to the healthcare consumer is also obtained, such as, but not limited to: services covered by each of two or more health care benefit plans to the healthcare consumer's projected healthcare service utilization to determine a percentage of projected healthcare services that would be covered by each of the candidate health insurance plans; the specific providers in each of the plans and/or a percentage of the healthcare consumer's presently used providers that are within the provider network of each of the plans; any restrictions on medication and therapy usage under each of the plans and/or how these restrictions may affect the healthcare consumer based on the healthcare consumer's present and predicted future health care service utilization; and any other criteria associated with each plan desired by the healthcare consumer and/or the provider of the process for healthcare benefit plan selection. In one embodiment, the healthcare consumer is provided data comparing these various other characteristics of each of the two or more candidate healthcare benefit plans. Consequently, in one embodiment, out-of-pocket cost is but one comparison criteria/characteristic and the healthcare consumer can weight the various comparison data to best meet his or her specific needs and/or circumstances.

Using the method and system for healthcare benefit plan selection disclosed herein, a healthcare consumer is provided a healthcare benefit plan recommendation that is based on the healthcare consumer's projected healthcare service utilization, as determined/predicted using the healthcare consumer's general/demographic data, the healthcare consumer's historical healthcare utilization data, and the healthcare consumer's personal health profile data. Consequently, using the method and system for healthcare benefit plan selection disclosed herein, the healthcare consumer is more likely to choose a healthcare benefit plan that will meet the healthcare consumer's current and future needs.

As discussed in more detail below, using the below embodiments, with little or no modification and/or user input, there is considerable flexibility, adaptability, and opportunity for customization to meet the specific needs of various users under numerous circumstances.

Common reference numerals are used throughout the FIG.s and the detailed description to indicate like elements. One skilled in the art will readily recognize that the above FIG.s are examples and that other architectures, modes of operation, orders of operation and elements/functions can be provided and implemented without departing from the characteristics and features of the invention, as set forth in the claims.

DETAILED DESCRIPTION

Embodiments will now be discussed with reference to the accompanying FIG.s, which depict one or more exemplary embodiments. Embodiments may be embodied in many different forms and should not be construed as limited to the embodiments set forth herein, shown in the FIG.s, and/or described below. Rather, these exemplary embodiments are provided to allow a complete disclosure that conveys the principles of the invention, as set forth in the claims, to those of skill in the art.

Some embodiments are implemented in a computing system including a conventional computing system running a conventional operating system such as those distributed by Microsoft Corporation of Redmond Wash.; Apple Computer Inc. of Cupertino Calif.; any Unix operating system; any Linux operating system; the Palm OS series of operating systems; or any other operating system designed to generally manage operations on a computing system, whether known at the time of filing or as developed later. Some embodiments are implemented in a mobile computing system running mobile operating systems such as Symbian® OS, Windows® Mobile, or any other operating system designed to generally manage operations on a mobile computing system, whether known at the time of filing or as developed later. As described more fully below, embodiments can be implemented on computing systems other than a conventional computing system such as, for example, a personal digital assistant, a cell phone, or other computing system capable of processing computer readable data, whether known at the time of filing or as developed later. Computing systems also include those in which one or more computing resources (hardware or software) are located remotely and accessed via network, such as a Local Area Network (LAN), Wide Area Network (WAN), a public network, such as the Internet, a private network, a combination of network types, a computing system bus, or other electronic medium in which data may be exchanged between one computing system and one or more other computing system(s), whether known at the time of filing or as developed later. Embodiments may be included as add-on software for existing software programs, packages or applications, and embodiments may be a feature of an application that is bundled with a computing system or sold separately. Some embodiments may also be implemented as functionality embedded in hardware devices and systems.

Output generated by one or more embodiments can be displayed on a display screen, delivered from a website and/or web-based function, transmitted to a remote device, stored on any database, computer server or other storage mechanism, printed, or used in any other way. In addition, in some embodiments, processes and/or systems described herein may make use of input provided to the computer device implementing a process and/or application, discussed herein, via user interface devices such as a keyboard, mouse, touchpad, or any other device capable of providing user input to a computing system or for translating user actions into computing system operations, whether known at the time of filing or as developed later.

Hardware System Architecture

Figure 1:
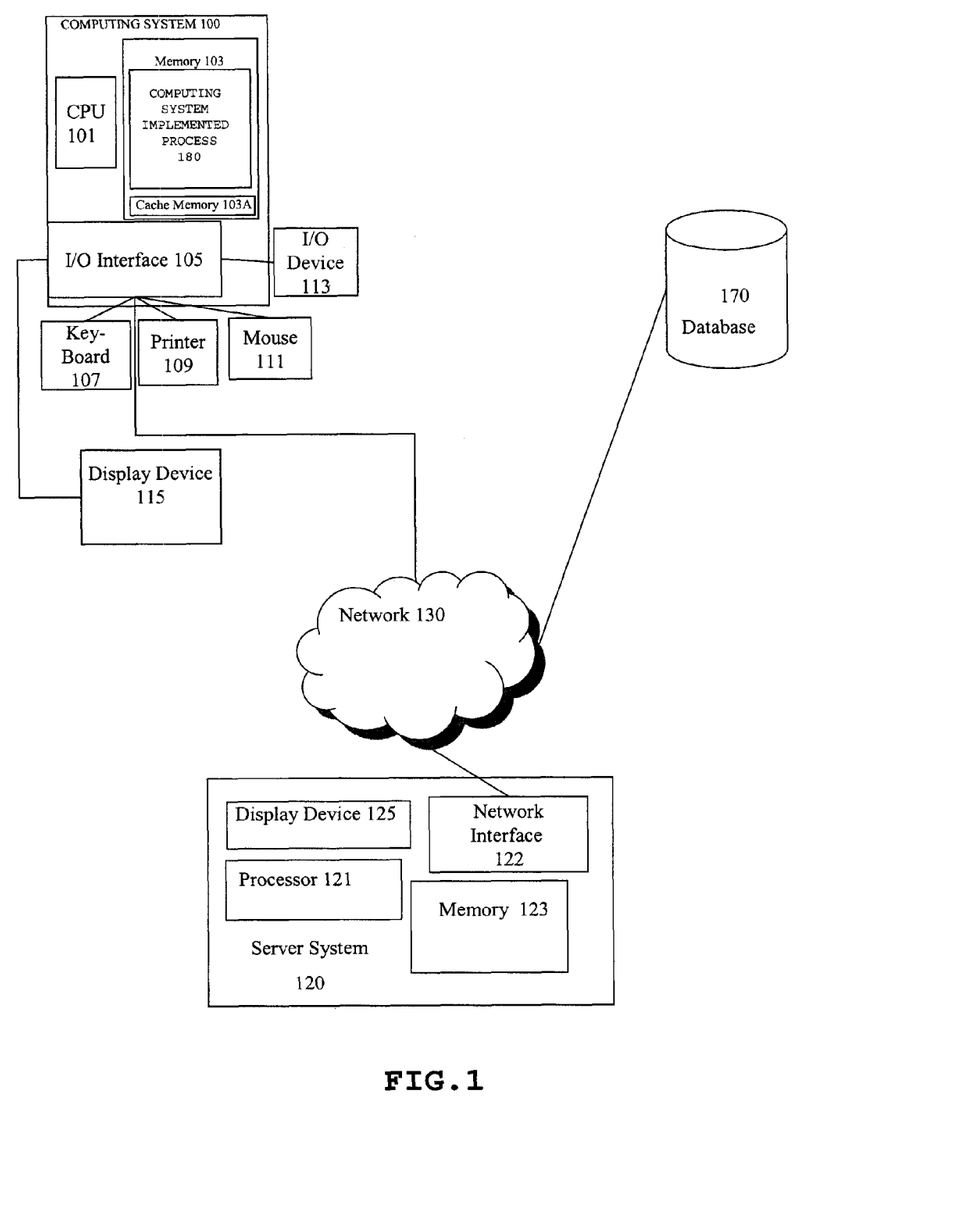
FIG. 1 is a block diagram of an exemplary hardware architecture for implementing one embodiment.

FIG. 1 is a block diagram of exemplary hardware architecture for implementing one embodiment of a process for healthcare benefit plan selection, such as exemplary processes for healthcare benefit plan selection 200, discussed below, that includes: a computing system 100; a server system 120; and a database 170, all operatively connected by a network 130.

As seen in FIG. 1, computing system 100 typically includes a processor 101, an input/output (I/O) interface 105, and a memory system 103, including cache memory 103A. In one embodiment, computing system 100 includes all or part of one or more computing system implemented processes 180 such as, but not limited to, a computing system implemented healthcare management system, a computing system implemented personal financial management system, a computing system implemented personal accounting system, and/or a computing system implemented tax management system that is a used by, is a parent system for, is accessed by, and/or is otherwise associated with, a process for healthcare benefit plan selection, such as exemplary processes for healthcare benefit plan selection 200.

Computing system 100 may further include standard user interface devices such as a keyboard 107, a mouse 111, a printer 109, and a display device 115, as well as, one or more standard input/output (I/O) devices 113, such as a compact disk (CD) or DVD drive, floppy disk drive, or other digital or waveform port, or other device capable of inputting data to, and outputting data from, computing system 100, whether known at the time of filing or as later developed. As discussed in more detail below, in one embodiment, a process for healthcare benefit plan selection, and/or one or more computing system implemented processes, can be loaded, in whole, or in part, into computing system 100 via I/O device 113, such as from a CD, DVD or floppy disk containing all, or part, of a process for healthcare benefit plan selection and/or a computing system implemented process. In one embodiment, a process for healthcare benefit plan selection, and/or one or more computing system implemented processes, can be loaded, in whole, or in part, into computing system 100 via one or more of the following: a healthcare management application; a healthcare management web-site; a healthcare financial management application; a healthcare financial management web-site; a health information application; a health information web-site; a health insurance application; and/or a health insurance web-site containing all, or part, of a process for healthcare benefit plan selection and/or a computing system implemented process.

Also shown in FIG. 1 is database 170. In one embodiment, database 170 is a designated server system or computing system, or a designated portion of a server system or computing system, such as computing systems 100 and 120. In one embodiment, database 170 is a dedicated mass storage device implemented in software, hardware, or a combination of hardware and software. In one embodiment, database 170 is a web-based function. As discussed in more detail below, in one embodiment, a process for healthcare benefit plan selection, and/or one or more computing system implemented processes, is/are stored in whole, or in part, in database 170.

In one embodiment, computing system 100 and database 170, are coupled to a server system 120 by network 130. Server system 120 typically includes a server system display device 125, a server system processor 121, a server system memory 123, and a server system network interface 122. As discussed in more detail below, in one embodiment, a process for healthcare benefit plan selection, and/or one or more computing system implemented processes, is/are stored in whole, or in part, in server system 120.

Network 130 can be any network or network system that is of interest to a user such as a Local Area Network (LAN), a Wide Area Network (WAN), a public network, such as the Internet, a private network, a combination of network types, or other network capable of allowing communication between two or more computing systems, whether known at the time of filing or as later developed. In various embodiments, server system network interface 122 and I/O interface 105 include analog modems, digital modems, a network interface card, a broadband connection, or any other means for communicably coupling computing system 100, database 170, and server system 120, via network 130, whether known at the time of filing or as later developed.

Those of skill in the art will readily recognize that the components shown in FIG. 1, such as computing system 100, database 170, server system 120, and their respective components, are shown for illustrative purposes only and that architectures with more or fewer components can implement, and benefit from, a process for healthcare benefit plan selection, such as exemplary process for healthcare benefit plan selection 200 discussed below. Moreover, one or more components of computing system 100, database 170, and server system 120 may be located remotely from their respective system and accessed via network, as discussed herein. In addition, the particular type of, and configuration of, computing systems 100, database 170, and server system 120 are not relevant.

As discussed in more detail below, in one embodiment, a process for healthcare benefit plan selection, and/or one or more computing system implemented processes, is/are stored in whole, or in part, in memory system 103 and/or cache memory 103A, of computing system 100, and/or in server memory system 123 of server system 120 and/or in database 170, and executed on computing system 100. As used herein, a memory refers to a volatile memory, a non-volatile memory, or any combination of the two.

Although a process for healthcare benefit plan selection, and/or one or more computing system implemented processes, can sometimes be referred to herein, alternatively, as a process, an application, a module, a program, a component of a software system, a component of a software package, a component of a parent system, or a feature of a parent system, this terminology is illustrative only. In some embodiments, a process for healthcare benefit plan selection, and/or one or more computing system implemented processes, is/are capable of being called from an application or the operating system. In one embodiment, an application or program is generally defined to be any executable code. Moreover, those of skill in the art will understand that when it is said that an application or an operation takes some action, the action is the result of executing one or more instructions by a processor, such as processor 101 or server system processor 121. In one embodiment, execution of a process for healthcare benefit plan selection, and/or one or more computing system implemented processes, by processor 101 or server system processor 121, results in the operations of an agent computer process (not shown) and/or a rule computer process (not shown).

In one embodiment, a process for healthcare benefit plan selection, and/or one or more computing system implemented processes, is/are a computer application or process implemented and/or run and/or stored, in full, or in part, in, or on, a computer program product. Herein, a computer program product comprises a medium configured to store and/or transport computer readable code, whether known at the time of filing or as later developed. Some examples of computer program products are CD-ROM discs, DVDs, ROM cards, floppy discs, magnetic tapes, computer hard drives, servers on a network, such as server system 120 of FIG. 1, and signals transmitted over a network, such as network 130 of FIG. 1, or other media or process capable of delivering computer readable data representing computer readable code, whether known at the time of filing or as later developed. This medium may belong to a computing system, such as computing system 100 of FIG. 1, described above. However, the medium also may be removed from the computing system.

For example, all, or part, of a process for healthcare benefit plan selection, and/or one or more computing system implemented processes, may be stored in a memory that is physically located in a location, such as server system memory 123, or database 170, of FIG. 1, different from a computing system, such as computing system 100 of FIG. 1, utilizing a process for healthcare benefit plan selection, and/or one or more computing system implemented processes. In one embodiment, all, or part, of a process for healthcare benefit plan selection, and/or one or more computing system implemented processes, may be stored in a memory that is physically located, separate from the computing system's processor(s), such as processor 101 of FIG. 1, and the computing system processor(s) can be coupled to the memory in a client-server system, such as server system 120 of FIG. 1, or, alternatively, via connection to another computer, such as computing system 100 of FIG. 1, via modems and analog lines, digital interfaces and a digital carrier line, or wireless or cellular connections.

In one embodiment, the computing system and/or server system, such as computing system 100 and/or server system 120 of FIG. 1, running and/or utilizing and/or storing all, or part, of a process for healthcare benefit plan selection, and/or one or more computing system implemented processes, is a portable computer, a workstation, a two-way pager, a cellular telephone, a smart phone, a digital wireless telephone, a personal digital assistant, a server computer, an Internet appliance, or any other device that includes components that can execute all, or part, of a process for healthcare benefit plan selection, and/or one or more computing system implemented processes, in accordance with at least one of the embodiments as described herein. Similarly, in another embodiment, a process for healthcare benefit plan selection, and/or one or more computing system implemented processes, is/are implemented on and/or run and/or stored on a computing system and/or server system that is comprised of multiple different computers, wireless devices, cellular telephones, digital telephones, two-way pagers, personal digital assistants, server computers, or any desired combination of these devices, that are interconnected to perform the processes as described herein.

Process

Herein, the terms "healthcare consumer", "user", and/or "consumer" are used interchangeably to denote a person who is entitled to benefits and/or service under a healthcare benefit plan. Herein, a healthcare consumer can be a primary and/or responsible party under a healthcare benefit plan and/or any dependents of the primary and/or responsible party and/or any other parties entitled to benefits and/or service under a healthcare benefit plan.

Herein, the term "healthcare" includes any general and/or specialized treatment, assessment, maintenance, therapy, medication, and/or advice relating to all, or any portion of, a healthcare consumer's state of health, including but not limited to: general medical, specialized medical, surgical, dental, vision, psychological, and/or any other type of treatment, assessment, maintenance, therapy, medication, and/or advice.

Herein, the term "healthcare benefit plan" and "health insurance plan" are used interchangeably to denote any policy, program, means and/or mechanism whereby a healthcare consumer is provided benefits and/or service and/or entitlements to healthcare.

Herein, the terms "healthcare benefit plan provider", "healthcare benefit plan sponsor", "employer" and/or "organization" are used to denote any individual party, organization, or group that provides, presents, offers, pays for, in whole or in part, or is otherwise associated with giving a healthcare consumer access to one or more healthcare benefit plans, health insurance, and/or healthcare expense account programs.

In accordance with one embodiment, a process for healthcare benefit plan selection determines a healthcare consumer's projected healthcare service utilization for a defined timeframe using a personalized healthcare service utilization model. In one embodiment, the personalized healthcare service utilization model is created using: general/demographic data associated with the healthcare consumer; the healthcare consumer's historical healthcare service utilization; and the healthcare consumer's personal health profile data.

In one embodiment, data associated with the rules governing the operation and use of two or more candidate healthcare benefit plans available to the healthcare consumer is also obtained. In one embodiment, the rules governing the operation and use of the two or more candidate healthcare benefit plans are then applied to healthcare consumer's projected healthcare service utilization for the defined timeframe to create expected healthcare consumer experience data under each of two or more candidate healthcare benefit plans. In one embodiment, the expected healthcare consumer experience data are then compared. In one embodiment, comparison data and/or a plan recommendation is then provided to the healthcare consumer.

Figure 2:
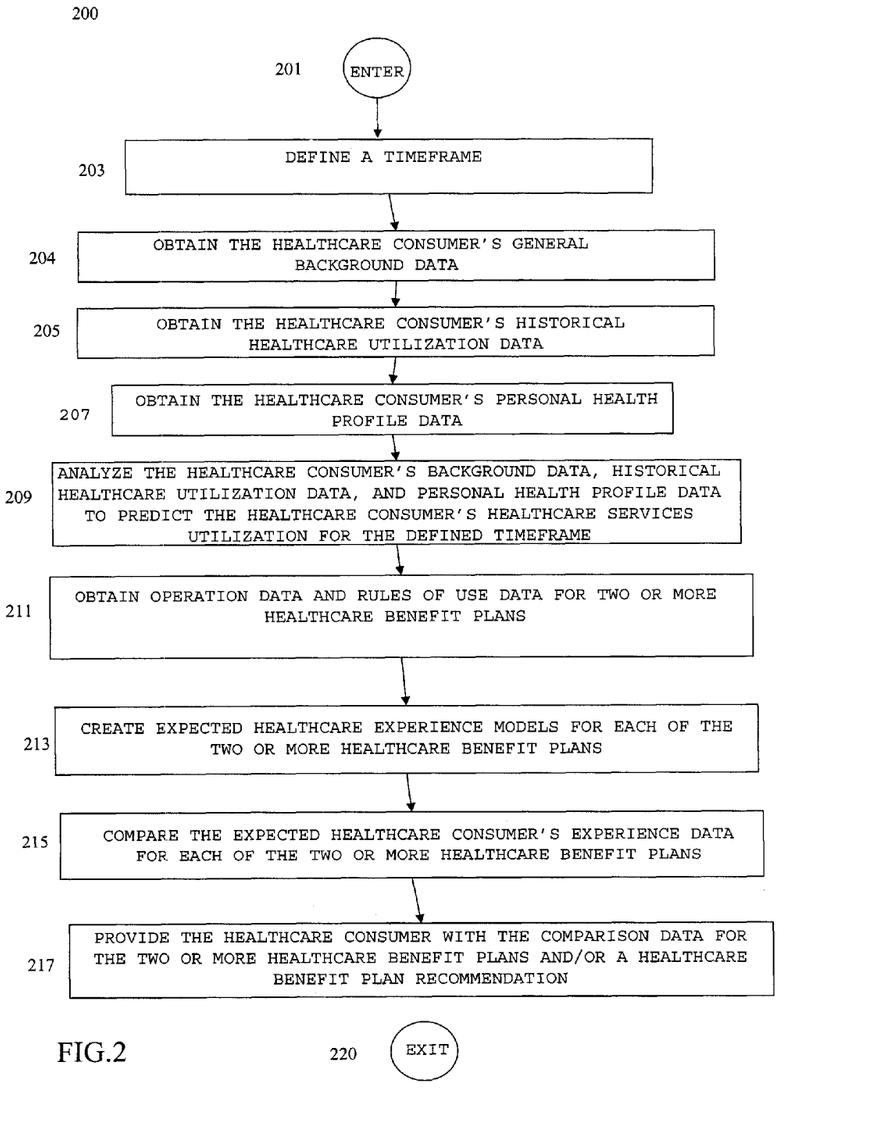
FIG. 2 is a flow chart depicting a process for healthcare benefit plan selection in accordance with one embodiment.

FIG. 2 a flow chart depicting a process for healthcare benefit plan selection 200 in accordance with one embodiment. Process for healthcare benefit plan selection 200 begins at ENTER OPERATION 201 of FIG. 2 and process flow proceeds to DEFINE A TIMEFRAME OPERATION 203.

In one embodiment, at DEFINE A TIMEFRAME OPERATION 203 a healthcare consumer and/or a provider of process for healthcare benefit plan selection 200 defines a timeframe of the analysis of process for healthcare benefit plan selection 200.

In one embodiment, the timeframe of DEFINE A TIMEFRAME OPERATION 203 is defined by the healthcare consumer implementing process for healthcare benefit plan selection 200. In one embodiment, the timeframe is set as a default value by the provider of process for healthcare benefit plan selection 200 with, in one embodiment, a healthcare consumer override feature.

In various embodiments, the timeframe of DEFINE A TIMEFRAME OPERATION 203 can be any period desired. In one embodiment, the defined timeframe is the time between open enrollment periods in an employer/organization sponsored healthcare benefit plan and/or a defined healthcare benefit plan year. In one embodiment, the timeframe can be set to shorter or longer periods such as, but not limited to: a month; a quarter; six months; a year; multiple years; a decade; multiple decades; a working lifetime; or any other timeframe desired by the healthcare consumer and/or the provider of process for healthcare benefit plan selection 200.

In one embodiment, the timeframe of DEFINE A TIMEFRAME OPERATION 203 is set by the healthcare consumer using a user interface device, such as a keyboard, mouse, touch pad, voice recognition software, or any other means and/or mechanism for converting user actions into computing system processes.

As discussed in more detail below, the timeframe chosen at DEFINE A TIMEFRAME OPERATION 203 is important not only because it defines the amount of time of interest, but also because it defines a stage in life for the healthcare consumer and, as discussed below, the healthcare consumer's stage in life is often highly determinative of the healthcare consumer's expected healthcare service utilization. As an example, a male healthcare consumer of age 25 who defines a timeframe of one year at DEFINE A TIMEFRAME OPERATION 203 is statistically less likely to incur healthcare expenses associated with an enlarged prostate than a male user of age 55 over the same period. In addition, some diseases/conditions are statically more likely to reveal themselves in certain stages of life such as young adult, middle age, old age etc. and, in some cases, once the critical stage of life/window has passed the likelihood of these conditions occurring drops off significantly. One very common example would be maternity expenses for a female healthcare consumer. Consequently, in one embodiment, the choice of timeframe at DEFINE A TIMEFRAME OPERATION 203 can be very significant and a controlling factor.

In one embodiment, once the timeframe is established at DEFINE A TIMEFRAME OPERATION 203, process flow proceeds to OBTAIN THE HEALTHCARE CONSUMER'S GENERAL BACKGROUND DATA OPERATION 204.

In one embodiment, at OBTAIN THE HEALTHCARE CONSUMER'S GENERAL BACKGROUND DATA OPERATION 204, data representing the healthcare consumer's general background, is obtained. Recall that, herein, the term healthcare consumer includes the primary healthcare consumer and/or any and/or all of the primary healthcare consumer's dependents to be enrolled in a healthcare benefit plan.

In one embodiment, the general background data includes general/demographic data about the healthcare consumer such as, but not limited to: the healthcare consumer's age; the healthcare consumer's sex; the healthcare consumer's occupation; the healthcare consumer's area of residence; the healthcare consumer's race and/or ethnic background; and/or any other general information about the healthcare consumer considered by the healthcare consumer, and/or any other party, to be significant and/or indicative of the healthcare consumer's future health. In addition, in one embodiment, at OBTAIN THE HEALTHCARE CONSUMER'S GENERAL BACKGROUND DATA OPERATION 204, data representing the recommended and/or average utilization of the average person of the healthcare consumer's background over the defined timeframe is obtained as well as any general health data/statistics associated with persons having backgrounds similar to the healthcare consumer.

As discussed in more detail below, the healthcare consumer's general background data obtained at OBTAIN THE HEALTHCARE CONSUMER'S GENERAL BACK- GROUND DATA OPERATION 204 is combined with other data discussed below to create a personalized projected healthcare service utilization model for the healthcare consumer. To this end, the healthcare consumer's general background data is helpful to predict the healthcare service utilization for an average person like the healthcare consumer over the defined timeframe and provide a generalized base usage model. For many currently available methods and processes for helping a healthcare consumer choose a healthcare plan, this is typically the total extent of analysis conducted.

In one embodiment, in addition to the healthcare consumer's general background data being obtained at OBTAIN THE HEALTHCARE CONSUMER'S GENERAL BACKGROUND DATA OPERATION 204, the healthcare consumer's historical healthcare utilization data is obtained at OBTAIN THE HEALTHCARE CONSUMER'S HISTORICAL HEALTHCARE UTILIZATION DATA OPERATION 205.

In one embodiment, the healthcare consumer's historical healthcare utilization data includes, but is not limited to: data representing the healthcare consumer's actual historical utilization of his or her healthcare program; whether or not the healthcare consumer actually takes advantage of regularly scheduled check ups and/or other preventative measures as would expected based on the healthcare consumer's general background data obtained at OBTAIN THE HEALTHCARE CONSUMER'S GENERAL BACKGROUND DATA OPERATION 204; whether the healthcare consumer follows and/or stays on any recommended routines, programs and medications; the healthcare consumer's family medical history; and/or the healthcare consumer's overall usage and historical attitude towards healthcare in general.

In one embodiment, at OBTAIN THE HEALTHCARE CONSUMER'S HISTORICAL HEALTHCARE UTILIZATION DATA OPERATION 205, data representing the healthcare consumer's actual historical utilization of his or her healthcare program and/or any historical healthcare related claims is obtained to analyze the healthcare consumer's specific healthcare utilization habits such as, previously claimed medical conditions, whether or not the healthcare consumer actually takes advantage of regularly scheduled check ups and/or other preventative measures, and/or whether the healthcare consumer follows and/or stays on any recommended routines, programs and medications. This data is not only valuable as used to estimate future preventative healthcare services to be used, but it can also be indicative of the healthcare consumer's "healthcare personality", that is to say, does the healthcare consumer take healthcare and/or his or her health seriously. A healthcare consumer's healthcare personality, in-and-of itself, can be highly determinative of future health related events. For instance, is the healthcare consumer likely to discover, and head off, the onset of potential health issues, or is the healthcare consumer likely to discover the issues only after they have fully manifested themselves, and perhaps only after a trip to the ER.

In one embodiment, at OBTAIN THE HEALTHCARE CONSUMER'S HISTORICAL HEALTHCARE UTILIZATION DATA OPERATION 205, data representing the healthcare consumer's family medical history is obtained. It has long been recognized that family history and genetics play a very significant role in an individual's health and pre-disposition to numerous diseases. Diabetes, heart disease, cancer, high blood pressure, and cholesterol are but a few of the numerous diseases that are known to have a significant genetic factor.

In one embodiment, at OBTAIN THE HEALTHCARE CONSUMER'S HISTORICAL HEALTHCARE UTILIZATION DATA OPERATION 205 any other data representing the healthcare consumer's historical healthcare utilization, including historical healthcare related claims, deemed significant and/or necessary and/or indicative of future health is obtained.

In one embodiment, in addition to the healthcare consumer's general background data being obtained at OBTAIN THE HEALTHCARE CONSUMER'S GENERAL BACKGROUND DATA OPERATION 204, and the healthcare consumer's historical healthcare utilization data being obtained at OBTAIN THE HEALTHCARE CONSUMER'S HISTORICAL HEALTHCARE UTILIZATION DATA OPERATION 205, healthcare consumer health profile data that is highly personalized and specific to the user is obtained at OBTAIN THE HEALTHCARE CONSUMER'S PERSONAL HEALTH PROFILE DATA OPERATION 207.

In one embodiment, the healthcare consumer's personal health profile data includes, but is not limited to, personal health profile data such as: existing disease, diagnoses, treatment programs; the likely result of a diagnosed healthcare consumer condition predicted based on the general disposition of the healthcare consumer to making use of available healthcare and/or following medical advice; trends/patterns in the healthcare consumer's specific medical history and/or lab and/or other clinical results; specific activities the healthcare consumer takes part in; the healthcare consumer's general activity level; and/or any other data that is indicative of health risks, health attitudes, and/or pre-dispositions to disease and/or injury specific to the healthcare consumer.

In one embodiment, at OBTAIN THE HEALTHCARE CONSUMER'S PERSONAL HEALTH PROFILE DATA OPERATION 207, data representing existing disease, diagnoses, treatment programs and the specific health of the healthcare consumer is obtained from clinical results and/or medical records. As discussed below, this data is used to predict future healthcare service utilization based on typical services needed to treat any of these conditions. In addition, in one embodiment, some of the data obtained at OBTAIN THE HEALTHCARE CONSUMER'S HISTORICAL HEALTHCARE UTILIZATION DATA OPERATION 205 regarding the healthcare consumer's actual historical utilization of healthcare services is used to predict how the healthcare consumer will respond/behave in light of these known conditions. As an example, a healthcare consumer diagnosed with high cholesterol who has shown a willingness to take prescribed medications and seek regular checkups will be likely to incur only the healthcare service needs associated with the prescribed medications and checkups for the condition. In contrast, a healthcare consumer with the same diagnosis who is not likely to take the prescribed medication and see the doctor regularly is more likely to suffer a heat attack and/or need by-pass surgery. In one embodiment, at OBTAIN THE HEALTHCARE CONSUMER'S PERSONAL HEALTH PROFILE DATA OPERATION 207, other data representing trends/patterns in the healthcare consumer's specific medical history and/or lab results are obtained and this data is used to predict future illness.

In one embodiment, at OBTAIN THE HEALTHCARE CONSUMER'S PERSONAL HEALTH PROFILE DATA OPERATION 207, data representing activities the healthcare consumer takes part in and the healthcare consumer's general activity level is obtained and used to predict future illness and/or injury. For instance, a healthcare consumer who takes part in strenuous activities like mountain biking or soccer is more likely to suffer broken limbs while a healthcare consumer who likes to watch TV is more likely to suffer from cardio-vascular problems. In one embodiment, at OBTAIN THE HEALTHCARE CONSUMER'S PERSONAL HEALTH PROFILE DATA OPERATION 207, any other data that is indicative of health risks and/or pre-dispositions to disease and/or injury specific to the healthcare consumer is obtained.

As with the other data obtained by process for healthcare benefit plan selection 200 discussed above, the data obtained at OBTAIN THE HEALTHCARE CONSUMER'S PERSONAL HEALTH PROFILE DATA OPERATION 207 might be, under other circumstances, considered highly personal, and in some cases it certainly is. However, it must be borne in mind that, in one embodiment, the data is not meant to be shared beyond those persons designated by the healthcare consumer and that the accuracy of the analysis using the data is highly beneficial to the goals of process for healthcare benefit plan selection 200 and the healthcare consumer.

Returning to FIG. 2, in one embodiment the healthcare consumer's general background data, the healthcare consumer's historical healthcare utilization data, and the healthcare consumer's personal health profile data is obtained at OBTAIN THE HEALTHCARE CONSUMER'S GENERAL BACKGROUND DATA OPERATION 204, OBTAIN THE HEALTHCARE CONSUMER'S HISTORICAL HEALTHCARE UTILIZATION DATA OPERATION 205, and OBTAIN THE HEALTHCARE CONSUMER'S PERSONAL HEALTH PROFILE DATA OPERATION 207, respectively, directly from the healthcare consumer and/or the healthcare consumer's medical records/files. In one embodiment, the healthcare consumer's general background data, the healthcare consumer's historical healthcare utilization data, and the healthcare consumer's personal health profile data is provided to process for healthcare benefit plan selection 200 by entering the data into a user interface displayed on a computing system, such as computing system 100 described above. In other embodiments, the healthcare consumer's general background data, the healthcare consumer's historical healthcare utilization data, and the healthcare consumer's personal health profile data is obtained by any means for obtaining, collecting, accessing, entering, transferring, relaying and/or providing data in any form, to a process, such as process for healthcare benefit plan selection 200, whether known at the time of filing or as developed thereafter.

For instance, in one embodiment, process for healthcare benefit plan selection 200 is part of a parent personal healthcare management, personal financial, business financial, accounting, or tax preparation software system, program, package or application, such as computing system implemented process 180 of FIG. 1, that implements, includes, is accessed by, and/or is otherwise associated with process for healthcare benefit plan selection 200 (FIG. 2). In these embodiments, the healthcare consumer's general background data, the healthcare consumer's historical healthcare utilization data, and the healthcare consumer's personal health profile data may be obtained directly from, or through, the parent computing system implemented software system, program, package or application, such as computing system implemented process 180 of FIG. 1.

Returning to FIG. 2, in one embodiment, the healthcare consumer's general background data, the healthcare consumer's historical healthcare utilization data, and the healthcare consumer's personal health profile data is obtained from invoices/patient bills and/or claim data provided to process for healthcare benefit plan selection 200, and or a parent computing system implemented process, by health care providers such as hospitals and/or doctors and/or other medical service personnel.

As discussed above, in one embodiment, process for healthcare benefit plan selection 200 is part of a parent personal healthcare management, personal financial, business financial, accounting, or tax preparation software system, program, package or application, such as computing system implemented process 180 of FIG. 1, that implements, includes, is accessed by, and/or is otherwise associated with process for healthcare benefit plan selection 200, as one of multiple features. Some of these parent systems provide the capability to obtain, receive, and/or process electronic copies of the invoices/claims, often in their specific formats, and then store the data for use by process for healthcare benefit plan selection 200 in one of numerous locations by one of numerous methods known to those of skill in the art.

In one embodiment, the healthcare consumer's general background data, the healthcare consumer's historical healthcare utilization data, and the healthcare consumer's personal health profile data is obtained from Explanation of Benefits (EOB) data provided to process for healthcare benefit plan selection 200 by a health insurance provider and/or the healthcare consumer.

According to one embodiment, the health insurance providers transfer electronic copies of the EOBs, often in specific formats, to the provider of process for healthcare benefit plan selection 200, and or a parent computing system implemented process. As noted above, in one embodiment, process for healthcare benefit plan selection 200 is part of a parent personal healthcare management, personal financial, business financial, accounting, or tax preparation software system, program, package or application, such as computing system implemented process 180 of FIG. 1, that implements, includes, is accessed by, and/or is otherwise associated with process for healthcare benefit plan selection 200. Some of these parent systems provide the capability to obtain, receive, and/or process electronic copies of the EOBs and then store the data for use by process for healthcare benefit plan selection 200 in one of numerous locations by one of numerous methods known to those of skill in the art.

In one embodiment, the healthcare consumer's general background data, the healthcare consumer's historical healthcare utilization data, and the healthcare consumer's personal health profile data is obtained from one or more of the following: a healthcare management system/application; a healthcare management web-site; a healthcare financial management system/application; a healthcare financial management web-site; a health information system/application; a health information web-site; a health insurance system/application; and/or a health insurance web-site.

In some embodiments, the healthcare consumer's general background data, the healthcare consumer's historical healthcare utilization data, and the healthcare consumer's personal health profile data is obtained from any combination of the above sources and/or from any other source of data, whether known at the time of filing or as developed thereafter.

In one embodiment, the healthcare consumer's general background data, the healthcare consumer's historical healthcare utilization data, and the healthcare consumer's personal health profile data is stored, in whole, or in part, in a database maintained by, accessible by, owned by, or otherwise related to, a provider of process for healthcare benefit plan selection 200 by any one of the numerous mechanisms known to those of skill in the art. For instance, in one embodiment, the data, in whole, or in part, is stored in a memory system, such as memory system 103 or server memory system 123, or database 170, of FIG. 1, or in a cache memory, such as cache memory 103A of FIG. 1, or in any main memory or mass memory, associated with a computing device, such as computing system 100 described above. In one embodiment, the data, in whole, or in part, is stored in any computing device and/or server system, such as computing system 100 or server system 120, or other device, in another location, or on/in a computer readable medium, and/or any other computer program product, as defined herein. In one embodiment, the data, in whole, or in part, is stored on a webpage, in a web-based system or on a public network such as the Internet.

Returning to FIG. 2, in some embodiments, the data stored as described above is maintained, in whole, or in part, by: the healthcare consumer; the provider of process for healthcare benefit plan selection 200; an investment service; a health insurance provider; a healthcare service provider; a third party data storage institution; any third party service or institution; or any other parties. In these embodiments, access to the healthcare consumer's personal health profile data is then granted to process for healthcare benefit plan selection 200 by providing access to the data and/or providing the data on a computer program product.

In other embodiments, the healthcare consumer's general background data, the healthcare consumer's historical healthcare utilization data, and the healthcare consumer's personal health profile data is provided through a network of computing systems and/or server systems that is comprised of multiple different computers, wireless devices, cellular telephones, digital telephones, two-way pagers, personal digital assistants, server computers, or any desired combination of these devices, that are interconnected using a network, such as network 130 of FIG. 1. As discussed above, network 130 can be any network or network system that is of interest to a user such as a Local Area Network (LAN), a Wide Area Network (WAN), a public network, such as the Internet, a private network, a combination of network types, or other network capable of allowing communication between two or more computing systems, whether available or known at the time of filing or as later developed.

In other embodiments, the healthcare consumer's general background data, the healthcare consumer's historical healthcare utilization data, and the healthcare consumer's personal health profile data is obtained/accessed/collected through e-mail or through text messaging. In other embodiments, the healthcare consumer's general background data, the healthcare consumer's historical healthcare utilization data, and the healthcare consumer's personal health profile data is provided to process for healthcare benefit plan selection 200 through any method, apparatus, process or mechanism for transferring data and/or text from one or more devices, computing systems, server systems, databases, web site/web functions and/or any devices having a data storage capability to one or more other devices, computing systems, server systems, databases, web site/web functions and/or any devices having a data storage capability, whether known at the time of filing or as thereafter developed.

In one embodiment, once: the healthcare consumer's general background data is obtained at OBTAIN THE HEALTHCARE CONSUMER'S GENERAL BACKGROUND DATA OPERATION 204; the healthcare consumer's historical healthcare utilization data is obtained at OBTAIN THE HEALTHCARE CONSUMER'S HISTORICAL HEALTHCARE UTILIZATION DATA OPERATION 205; and the healthcare consumer's personal health profile data is obtained at OBTAIN THE HEALTHCARE CONSUMER'S PERSONAL HEALTH PROFILE DATA OPERATION 207, process flow proceeds to ANALYZE THE HEALTHCARE CONSUMER'S BACKGROUND DATA, HISTORICAL HEALTHCARE UTILIZATION DATA, AND PERSONAL HEALTH PROFILE DATA TO PREDICT THE HEALTHCARE CONSUMER'S HEALTHCARE SERVICES UTILIZATION FOR THE DEFINED TIMEFRAME OPERATION 209.

In one embodiment at ANALYZE THE HEALTHCARE CONSUMER'S BACKGROUND DATA, HISTORICAL HEALTHCARE UTILIZATION DATA, AND PERSONAL HEALTH PROFILE DATA TO PREDICT THE HEALTHCARE CONSUMER'S HEALTHCARE SERVICES UTILIZATION FOR THE DEFINED TIMEFRAME OPERATION 209, the healthcare consumer's general background data obtained at OBTAIN THE HEALTHCARE CONSUMER'S GENERAL BACKGROUND DATA OPERATION 204, the healthcare consumer's historical healthcare utilization data obtained at OBTAIN THE HEALTHCARE CONSUMER'S HISTORICAL HEALTHCARE UTILIZATION DATA OPERATION 205, and the healthcare consumer's specific personal health profile data obtained at OBTAIN THE HEALTHCARE CONSUMER'S PERSONAL HEALTH PROFILE DATA OPERATION 207 is analyzed to create a personalized projected healthcare service utilization model for the healthcare consumer.

In one embodiment, the personalized projected healthcare service utilization model is created by using all, or part, of the data obtained at: OBTAIN THE HEALTHCARE CONSUMER'S GENERAL BACKGROUND DATA OPERATION 204; OBTAIN THE HEALTHCARE CONSUMER'S HISTORICAL HEALTHCARE UTILIZATION DATA OPERATION 205; and OBTAIN THE HEALTHCARE CONSUMER'S PERSONAL HEALTH PROFILE DATA OPERATION 207. In one embodiment, the data is combined with, processed by, analyzed by, and/or reviewed by experts in the medical field, healthcare professionals, insurance experts, actuaries, and any other persons, groups, programs, applications, processes, means mechanisms and/or institutions capable of analyzing health data and making predictions of future health events based on the data to create the personalized projected healthcare service utilization model.

In one embodiment, the personalized projected healthcare service utilization model created at ANALYZE THE HEALTHCARE CONSUMER'S BACKGROUND DATA, HISTORICAL HEALTHCARE UTILIZATION DATA, AND PERSONAL HEALTH PROFILE DATA TO PREDICT THE HEALTHCARE CONSUMER'S HEALTHCARE SERVICES UTILIZATION FOR THE DEFINED TIMEFRAME OPERATION 209 is used to predict the healthcare consumer's likely healthcare service utilization for the timeframe defined at DEFINE A TIMEFRAME OPERATION 203.

In one embodiment, the healthcare consumer's likely healthcare service utilization data is presented as a listing of services likely to be used over the defined timeframe based on the data provided. In one embodiment, this listing includes all regularly scheduled services the healthcare consumer is likely to use along with services the user is predicted to use based on his or her more specific and personal health profile data as obtained by process for healthcare benefit plan selection 200.

Methods, means, mechanisms and processes for developing a utilization model based on input data, such as a personalized projected healthcare service utilization model based on the data obtained by process for healthcare benefit plan selection 200, are well known to those of skill in the art. In addition, the specific use of the data and the operation of a given personalized projected healthcare service utilization model, will vary from user-to-user, application-to-application, embodiment-to-embodiment, and model developer-to-model developer. Consequently, a more detailed description of specific methods, means, mechanisms and processes for developing a utilization model based on input data, such as a personalized projected healthcare service utilization model based on data obtained by process for healthcare benefit plan selection 200, is omitted here to avoid detracting from the invention.

In one embodiment, once the personalized projected healthcare service utilization model for the healthcare consumer is used to predict the healthcare consumer's healthcare service utilization for the defined timeframe, predicted healthcare service utilization data representing the healthcare consumer's predicted healthcare service utilization for the defined timeframe is stored, in whole, or in part, in a database maintained by, accessible by, owned by, or otherwise related to, a provider of process for healthcare benefit plan selection 200 by any one of the numerous mechanisms known to those of skill in the art. For instance, in one embodiment, the data, in whole, or in part, is stored in a memory system, such as memory system 103 or server memory system 123, or database 170, of FIG. 1, or in a cache memory, such as cache memory 103A of FIG. 1, or in any main memory or mass memory, associated with a computing device, such as computing system 100 described above. In one embodiment, the data, in whole, or in part, is stored in any computing device and/or server system, such as computing system 100 or server system 120, or other device, in another location, or on/in a computer readable medium, and/or any other computer program product, as defined herein. In one embodiment, the data, in whole, or in part, is stored on a webpage, in a web-based system or on a public network such as the Internet.

Returning to FIG. 2, in some embodiments, the data stored as described above is maintained, in whole, or in part, by: the healthcare consumer; the provider of process for healthcare benefit plan selection 200; an investment service; a health insurance provider; a healthcare service provider; a third party data storage institution; any third party service or institution; or any other parties. In these embodiments, access to the data representing the healthcare consumer's predicted healthcare service utilization for the defined timeframe is then granted to process for healthcare benefit plan selection 200 at OBTAIN THE HEALTHCARE CONSUMER'S PERSONAL HEALTH PROFILE DATA OPERATION 207 by providing access to the data and/or providing the data on a computer program product.

In other embodiments, predicted healthcare service utilization data representing the healthcare consumer's predicted healthcare service utilization for the defined timeframe is provided through a network of computing systems and/or server systems that is comprised of multiple different computers, wireless devices, cellular telephones, digital telephones, two-way pagers, personal digital assistants, server computers, or any desired combination of these devices, that are interconnected using a network, such as network 130 of FIG. 1. As discussed above, network 130 can be any network or network system that is of interest to a user such as a Local Area Network (LAN), a Wide Area Network (WAN), a public network, such as the Internet, a private network, a combination of network types, or other network capable of allowing communication between two or more computing systems, whether available or known at the time of filing or as later developed.

In other embodiments, the predicted healthcare service utilization data representing the healthcare consumer's predicted healthcare service utilization for the defined timeframe is obtained/accessed/collected through e-mail or through text messaging. In other embodiments, the predicted healthcare service utilization data representing the healthcare consumer's predicted healthcare service utilization for the defined timeframe is provided to process for healthcare benefit plan selection 200 through any method, apparatus, process or mechanism for transferring data and/or text from one or more devices, computing systems, server systems, databases, web site/web functions and/or any devices having a data storage capability to one or more other devices, computing systems, server systems, databases, web site/web functions and/or any devices having a data storage capability, whether known at the time of filing or as thereafter developed.

In one embodiment, once the personalized projected healthcare service utilization model for the healthcare consumer is used to create predicted healthcare service utilization data for the defined timeframe at ANALYZE THE HEALTHCARE CONSUMER'S BACKGROUND DATA, HISTORICAL HEALTHCARE UTILIZATION DATA, AND PERSONAL HEALTH PROFILE DATA TO PREDICT THE HEALTHCARE CONSUMER'S HEALTHCARE SERVICES UTILIZATION FOR THE DEFINED TIMEFRAME OPERATION 209, process flow proceeds to OBTAIN OPERATION DATA AND RULES OF USE DATA FOR TWO OR MORE HEALTHCARE BENEFIT PLANS OPERATION 211.

In one embodiment, at OBTAIN OPERATION DATA AND RULES OF USE DATA FOR. TWO OR MORE HEALTHCARE BENEFIT PLANS OPERATION 211 process for healthcare benefit plan selection 200 obtains healthcare benefit plan operation data indicating the specific rules governing the operation and use of two or more candidate healthcare benefit plans available to the healthcare consumer. In one embodiment, the healthcare benefit plan operation data includes, but is not limited to: a description and/or listing of the benefits offered under each plan; a description and/or listing of the financial obligation of the healthcare consumer under each plan, i.e., deductibles, co-payments, and healthcare consumer responsibility for different types of procedures, under each plan; the specific providers, the number of providers and the area of the provider network in each plan; how healthcare expense account programs work within each plan; and/or data representing any other criteria and/or considerations associated with each plan as desired/defined by the healthcare consumer and/or the provider of the process for healthcare benefit plan selection.

In one embodiment, process for healthcare benefit plan selection 200 obtains healthcare benefit plan operation data indicating the specific rules governing the operation use of two or more candidate healthcare benefit plans available to the healthcare consumer at OBTAIN OPERATION DATA AND RULES OF USE DATA FOR TWO OR MORE HEALTHCARE BENEFIT PLANS OPERATION 211 by any of the means, mechanisms, methods and/or processes known in the art and/or as discussed herein, whether known at the time of filing, or as developed thereafter, either through public data or from the healthcare benefit plan and/or program providers.

In one embodiment, once process for healthcare benefit plan selection 200 obtains healthcare benefit plan operation data indicating the specific rules governing the operation use of two or more candidate healthcare benefit plans available to the healthcare consumer at OBTAIN OPERATION DATA AND RULES OF USE DATA FOR TWO OR MORE HEALTHCARE BENEFIT PLANS OPERATION 211, process flow proceeds to CREATE EXPECTED HEALTHCARE EXPERIENCE MODELS FOR EACH OF THE TWO OR MORE HEALTHCARE BENEFIT PLANS OPERATION 213.

In one embodiment, at CREATE EXPECTED HEALTHCARE EXPERIENCE MODELS FOR EACH OF THE TWO OR MORE HEALTHCARE BENEFIT PLANS OPERATION 213 the specific rules governing the operation use of two or more candidate healthcare benefit plans available to the healthcare consumer of OBTAIN OPERATION DATA AND RULES OF USE DATA FOR. TWO OR MORE HEALTHCARE BENEFIT PLANS OPERATION 211 are applied to healthcare consumer's predicted healthcare service utilization data for the defined timeframe of ANALYZE THE HEALTHCARE CONSUMER'S BACKGROUND DATA, HISTORICAL HEALTHCARE UTILIZATION DATA, AND PERSONAL HEALTH PROFILE DATA TO PREDICT THE HEALTHCARE CONSUMER'S HEALTHCARE SERVICES UTILIZATION FOR THE DEFINED TIMEFRAME OPERATION 209 to create expected healthcare consumer's experience data under each of two or more candidate healthcare benefit plans.

In various embodiments, the expected healthcare consumer's experience data shows various aspects of the expected healthcare consumer's experience under a given candidate healthcare benefit plan such as, but not limited to, one or more of the following: what, and/or what percentage, and/or what specific healthcares services, of the healthcare services the healthcare consumer is predicted to utilize by ANALYZE THE HEALTHCARE CONSUMER'S BACKGROUND DATA, HISTORICAL HEALTHCARE UTILIZATION DATA, AND PERSONAL HEALTH PROFILE DATA TO PREDICT THE HEALTHCARE CONSUMER'S HEALTHCARE SERVICES UTILIZATION FOR THE DEFINED TIMEFRAME OPERATION 209 are covered under each plan; the financial obligation the healthcare consumer is predicted to incur under each plan based on the healthcare services the healthcare consumer is predicted to utilize by ANALYZE THE HEALTHCARE CONSUMER'S BACKGROUND DATA, HISTORICAL HEALTHCARE UTILIZATION DATA, AND PERSONAL HEALTH PROFILE DATA TO PREDICT THE HEALTHCARE CONSUMER'S HEALTHCARE SERVICES UTILIZATION FOR THE DEFINED TIMEFRAME OPERATION 209; the number, and/or percentage, and/or specific providers, of the healthcare consumer's presently used providers are in each plan; how the healthcare consumer's other healthcare expense account programs will work within each plan; and/or data representing any other criteria and/or considerations associated with each plan as desired/defined by the healthcare consumer and/or the provider of the process for healthcare benefit plan selection.

In one embodiment, the expected healthcare consumer's experience data is used to generate data indicating various aspects of the expected healthcare consumer's experience for various specific healthcare benefit plans such as a PPO program, an HMO program, a user-sponsored program, an employer-sponsored program, Federal, State or Local Healthcare benefit plans, etc. This feature allows the healthcare consumer to obtain data for various programs in order to make a best fit choice. This feature can also provide the healthcare consumer with a more realistic analysis over time. For instance, an employer sponsored healthcare benefits plan may only be available while the healthcare consumer is employed, then the healthcare consumer must depend on personal and/or government plans. Consequently, if the timeframe defined at DEFINE A TIMEFRAME OPERATION 203 includes an expected change of employment status event, an accurate analysis must include the change in healthcare consumer costs for the predicted healthcare services utilization under the new plan and/or any change in cost of the plan itself.

Methods, means, mechanisms and processes for developing an operation/experience model based on input data and/or criteria are well known to those of skill in the art. In addition, the specific use of the data and the operation of a given expected healthcare consumer experience model, will vary from user-to-user, application-to-application, embodiment-to-embodiment, and model developer-to-model developer, and healthcare benefits plan-to-healthcare benefits plan. Consequently, a more detailed description of specific methods, means, mechanisms and processes for developing one or more expected healthcare consumer experience models and/or data is omitted here to avoid detracting from the invention.

In one embodiment, once the operation data and the specific rules governing the operation and use of the two or more candidate healthcare benefit plans are applied to the predicted healthcare service utilization data for the defined timeframe to create expected healthcare consumer's experience data under each of two or more candidate healthcare benefit plans at CREATE EXPECTED HEALTHCARE EXPERIENCE MODELS FOR EACH OF THE TWO OR MORE HEALTHCARE BENEFIT PLANS OPERATION 213, process flow proceeds to COMPARE THE EXPECTED HEALTHCARE CONSUMER'S EXPERIENCE DATA FOR EACH OF THE TWO OR MORE HEALTHCARE BENEFIT PLANS OPERATION 215.

In one embodiment, at COMPARE THE EXPECTED HEALTHCARE CONSUMER'S EXPERIENCE DATA FOR EACH OF THE TWO OR MORE HEALTHCARE BENEFIT PLANS OPERATION 215, the expected healthcare consumer's experience data indicating various characteristics of the expected healthcare consumer's experience under a given candidate healthcare benefit plan generated by the expected healthcare consumer experience models of CREATE EXPECTED HEALTHCARE EXPERIENCE MODELS FOR EACH OF THE TWO OR MORE HEALTHCARE BENEFIT PLANS OPERATION 213 is compared.

In one embodiment, expected healthcare consumer's experience comparison data indicating various aspects and/or differences in the expected healthcare consumer's experience under a given candidate healthcare benefit plan is generated and/or formatted in any one of numerous formats known in the art and/or as desired/defined by the healthcare consumer and/or the provider of process for healthcare benefit plan selection 200.

As noted above, in one embodiment, the healthcare consumer's predicted healthcare service utilization data for the defined timeframe of ANALYZE THE HEALTHCARE CONSUMER'S BACKGROUND DATA, HISTORICAL HEALTHCARE UTILIZATION DATA, AND PERSONAL HEALTH PROFILE DATA TO PREDICT THE HEALTHCARE CONSUMER'S HEALTHCARE SERVICES UTILIZATION FOR THE DEFINED TIMEFRAME OPERATION 209 is used to determine/predict the healthcare consumer's out-of pocket costs. As also noted above, in one embodiment, the healthcare consumer's predicted healthcare service utilization data is presented at ANALYZE THE HEALTHCARE CONSUMER'S BACKGROUND DATA, HISTORICAL HEALTHCARE UTILIZATION DATA, AND PERSONAL HEALTH PROFILE DATA TO PREDICT THE HEALTHCARE CONSUMER'S HEALTHCARE SERVICES UTILIZATION FOR THE DEFINED TIMEFRAME OPERATION 209 as a listing of services likely to be used over the defined timeframe based on the data provided through process for healthcare benefit plan selection 200. In this embodiment, at CREATE EXPECTED HEALTHCARE EXPERIENCE MODELS FOR EACH OF THE TWO OR MORE HEALTHCARE BENEFIT PLANS OPERATION 213 the cumulative healthcare consumer's out-of-pocket cost for these services is calculated by summing the individual service costs that would be incurred when the services are rendered under a given healthcare program as calculated using the data of OBTAIN OPERATION DATA AND RULES OF USE DATA FOR TWO OR MORE HEALTHCARE BENEFIT PLANS OPERATION 211.

Methods, means, mechanisms, devices, and processes for comparing and/or formatting comparison data are well known to those of skill in the art. In addition, the specific of comparison data and the operation of a given comparison means, will vary from user-to-user, application-to-application, embodiment-to-embodiment, and developer-to-developer. Consequently, a more detailed description of specific methods, means, mechanisms, devices, and processes for comparing and/or formatting comparison data is omitted here to avoid detracting from the invention.

In one embodiment, once the expected healthcare consumer's experience data indicating various aspects of the expected healthcare consumer's experience under a given candidate healthcare benefit plan generated by expected healthcare consumer experience model data of CREATE EXPECTED HEALTHCARE EXPERIENCE MODELS FOR EACH OF THE TWO OR MORE HEALTHCARE BENEFIT PLANS OPERATION 213 are compared, and/or comparison data is generated and formatted, at COMPARE THE EXPECTED HEALTHCARE CONSUMER'S EXPERIENCE DATA FOR EACH OF THE TWO OR MORE HEALTHCARE BENEFIT PLANS OPERATION 215, process flow proceeds to PROVIDE THE HEALTHCARE CONSUMER WITH THE COMPARISON DATA FOR THE TWO OR MORE HEALTHCARE BENEFIT PLANS AND/OR A HEALTHCARE BENEFIT PLAN RECOMMENDATION OPERATION 217.

In one embodiment, at PROVIDE THE HEALTHCARE CONSUMER WITH THE COMPARISON DATA FOR THE TWO OR MORE HEALTHCARE BENEFIT PLANS AND/OR A HEALTHCARE BENEFIT PLAN RECOMMENDATION OPERATION 217 all, or part of, the comparison data of COMPARE THE EXPECTED HEALTHCARE CONSUMER'S EXPERIENCE DATA FOR EACH OF THE TWO OR MORE HEALTHCARE BENEFIT PLANS OPERATION 215 and/or a healthcare plan recommendation is provided to the healthcare consumer.

In one embodiment, the comparison data and/or a healthcare plan recommendation is provided to the healthcare consumer by storing the data in whole, or in part, in a database maintained by, accessible by, owned by, or otherwise related to, the healthcare consumer and/or a provider of process for healthcare benefit plan selection 200 by any one of the numerous mechanisms known to those of skill in the art and/or as discussed herein and granting the healthcare consumer access to the data and/or providing the data on a computer program product.

In other embodiments, the comparison data and/or a healthcare plan recommendation is provided to the healthcare consumer through a network of computing systems and/or server systems that is comprised of multiple different computers, wireless devices, cellular telephones, digital telephones, two-way pagers, personal digital assistants, server computers, or any desired combination of these devices, that are interconnected using a network, such as network 130 of FIG. 1. As discussed above, network 130 can be any network or network system that is of interest to a user such as a Local Area Network (LAN), a Wide Area Network (WAN), a public network, such as the Internet, a private network, a combination of network types, or other network capable of allowing communication between two or more computing systems, whether available or known at the time of filing or as later developed.

In other embodiments, the comparison data and/or a healthcare plan recommendation is provided to the healthcare consumer through e-mail or through text messaging. In other embodiments, the comparison data and/or a healthcare plan recommendation is provided to the healthcare consumer through any method, apparatus, process or mechanism for transferring data and/or text from one or more devices, computing systems, server systems, databases, web site/web functions and/or any devices having a data storage capability to one or more other devices, computing systems, server systems, databases, web site/web functions and/or any devices having a data storage capability, whether known at the time of filing or as thereafter developed.

In one embodiment, once all, or part of, the comparison data of COMPARE THE EXPECTED HEALTHCARE CONSUMER'S EXPERIENCE DATA FOR EACH OF THE TWO OR MORE HEALTHCARE BENEFIT PLANS OPERATION 215 and/or a healthcare plan recommendation is provided to the healthcare consumer at PROVIDE THE HEALTHCARE CONSUMER WITH THE COMPARISON DATA FOR THE TWO OR MORE HEALTHCARE BENEFIT PLANS AND/OR A HEALTHCARE BENEFIT PLAN RECOMMENDATION OPERATION 217, process flow proceeds to EXIT OPERATION 220.

In one embodiment, at EXIT OPERATION 220 process for healthcare benefit plan selection 200 is exited to await new data.

Using process for healthcare benefit plan selection 200, a healthcare consumer is provided a healthcare benefit plan recommendation that is based on the healthcare consumer's projected healthcare service utilization, as determined/predicted using the healthcare consumer's general/demographic data, the healthcare consumer's historical healthcare utilization data, and the healthcare consumer's personal health profile data and/or healthcare personality profile.

Consequently, using process for healthcare benefit plan selection 200, the healthcare consumer is more likely to choose a healthcare benefit plan that will meet the healthcare consumer's current and future needs.

As discussed in more detail above, using the above embodiments, with little or no modification and/or user input, there is considerable flexibility, adaptability, and opportunity for customization to meet the specific needs of various users under numerous circumstances.

The present invention has been described in particular detail with respect to specific possible embodiments. Those of skill in the art will appreciate that the invention may be practiced in other embodiments. For example, the nomenclature used for components, capitalization of component designations and terms, the attributes, data structures, or any other programming or structural aspect is not significant, mandatory, or limiting, and the mechanisms that implement the invention or its features can have various different names, formats, and/or protocols. Further, the system and/or functionality of the invention may be implemented via various combinations of software and hardware, as described, or entirely in hardware elements. Also, particular divisions of functionality between the various components described herein are merely exemplary, and not mandatory or significant. Consequently, functions performed by a single component may, in other embodiments, be performed by multiple components, and functions performed by multiple components may, in other embodiments, be performed by a single component.

Some portions of the above description present the features of the present invention in terms of algorithms and symbolic representations of operations, or algorithm-like representations, of operations on information/data. These algorithmic and/or algorithm-like descriptions and representations are the means used by those of skill in the art to most effectively and efficiently convey the substance of their work to others of skill in the art. These operations, while described functionally or logically, are understood to be implemented by computer programs and/or computing systems. Furthermore, it has also proven convenient at times to refer to these arrangements of operations as steps or modules or by functional names, without loss of generality.

Unless specifically stated otherwise, as would be apparent from the above discussion, it is appreciated that throughout the above description, discussions utilizing terms such as "defining", "accessing", "analyzing", "obtaining", "determining", "collecting", "creating", "transferring", "storing", "comparing", "providing", etc., refer to the action and processes of a computing system or similar electronic device that manipulates and operates on data represented as physical (electronic) quantities within the computing system memories, resisters, caches or other information storage, transmission or display devices.

Certain aspects of the present invention include process steps or operations and instructions described herein in an algorithmic and/or algorithmic-like form. It should be noted that the process steps and/or operations and instructions of the present invention can be embodied in software, firmware, and/or hardware, and when embodied in software, can be downloaded to reside on and be operated from different platforms used by real time network operating systems.

The present invention also relates to an apparatus or system for performing the operations described herein. This apparatus or system may be specifically constructed for the required purposes, or the apparatus or system can comprise a general purpose system selectively activated or configured/reconfigured by a computer program stored on a computer program product as defined herein that can be accessed by a computing system or other device.

Those of skill in the art will readily recognize that the algorithms and operations presented herein are not inherently related to any particular computing system, computer architecture, computer or industry standard, or any other specific apparatus. Various general purpose systems may also be used with programs in accordance with the teaching herein, or it may prove more convenient/efficient to construct more specialized apparatuses to perform the required operations described herein. The required structure for a variety of these systems will be apparent to those of skill in the art, along with equivalent variations. In addition, the present invention is not described with reference to any particular programming language and it is appreciated that a variety of programming languages may be used to implement the teachings of the present invention as described herein, and any references to a specific language or languages are provided for illustrative purposes only and for enablement of the contemplated best mode of the invention at the time of filing.

The present invention is well suited to a wide variety of computer network systems operating over numerous topologies. Within this field, the configuration and management of large networks comprise storage devices and computers that are communicatively coupled to similar and/or dissimilar computers and storage devices over a private network, a LAN, a WAN, a private network, or a public network, such as the Internet.

It should also be noted that the language used in the specification has been principally selected for readability, clarity and instructional purposes, and may not have been selected to delineate or circumscribe the inventive subject matter.

Accordingly, the disclosure of the present invention is intended to be illustrative, but not limiting, of the scope of the invention, which is set forth in the claims below.

In addition, the operations shown in the FIG.s are identified using a particular nomenclature for ease of description and understanding, but other nomenclature is often used in the art to identify equivalent operations.

Therefore, numerous variations, whether explicitly provided for by the specification or implied by the specification or not, may be implemented by one of skill in the art in view of this disclosure.

What is claimed is:

1. A computer program product for providing a process for healthcare benefit plan selection comprising:
   a nontransitory computer readable medium;
   and computer program code, encoded on the computer readable medium, comprising computer readable instructions for:
   defining a timeframe;
   obtaining actual general/demographic data of a healthcare consumer;
   obtaining actual historical healthcare service utilization data of the healthcare consumer;
   obtaining actual personal health profile data of the healthcare consumer wherein the personal health profile data associated with the healthcare consumer comprises data indicating one or more of the healthcare consumer's activities;
   analyzing the actual general/demographic data, the actual historical healthcare service utilization data, and the actual personal health profile data of the healthcare consumer to create predicted healthcare services utilization data, the predicted healthcare services utilization data comprising specific healthcare services the healthcare consumer is likely to utilize during the defined timeframe wherein the predicted healthcare services utilization data is at least partly derived through the analysis of the healthcare consumer's activities, wherein the process is further configured to consider whether the healthcare consumer is likely to benefit from or suffer from illnesses or conditions resulting from athletic activities indicated in the personal health profile data;
   obtaining data associated with the rules governing the operation and of use of two or more healthcare benefit plans;
   creating expected healthcare experience data for each of the two or more healthcare benefit plans using the predicted healthcare services utilization data and the data associated with the rules governing the operation and of use of two or more healthcare benefit plans;
   comparing the expected healthcare experience data for each of the two or more healthcare benefit plans; and
   providing selection data to the healthcare consumer, the selection data being based, at least in part, on the comparison of the expected healthcare experience data for each of the two or more healthcare benefit plans, the selection data being used by the healthcare consumer to assist the healthcare consumer in selecting at least one of the two or more healthcare benefit plans.

2. The computer program product for providing a process for healthcare benefit plan selection of claim 1, wherein;
the selection data comprises a recommendation as to which one or more of the two or more healthcare benefit plans the healthcare consumer should select.

3. The computer program product for providing a process for healthcare benefit plan selection of claim 1, wherein;
the selection data comprises data representing the comparison of the expected healthcare experience data for each of the two or more healthcare benefit plans.

4. The computer program product for providing a process for healthcare benefit plan selection of claim 1, wherein;
the historical healthcare service utilization data associated with the healthcare consumer comprises data indicating the healthcare consumer's inclination to utilize preventative/maintenance healthcare services, further wherein;
the predicted healthcare services utilization data is based, at least in part, on the data indicating the healthcare consumer's inclination to utilize preventative/maintenance healthcare services.

5. The computer program product for providing a process for healthcare benefit plan selection of claim 1, wherein;
the personal health profile data associated with the healthcare consumer comprises data indicating the healthcare consumer's pre-disposition to injury and/or disease based on the healthcare consumer's historical attitude toward healthcare services utilization, further wherein;
the predicted healthcare services utilization data is based, at least in part, on the healthcare consumer's historical attitude toward healthcare services utilization.

6. The computer program product for providing a process for healthcare benefit plan selection of claim 1, wherein;
the personal health profile data associated with the healthcare consumer comprises data indicating the healthcare consumer's pre-disposition to injury and/or disease based on the healthcare consumer's family history, further wherein;
the predicted healthcare services utilization data is based, at least in part, on the healthcare consumer's family history.

7. The computer program product for providing a process for healthcare benefit plan selection of claim 1, wherein;
the expected healthcare experience data for each of the two or more healthcare benefit plans comprises expected healthcare consumer out-of-pocket costs.

8. The computer program product for providing a process for healthcare benefit plan selection of claim 1, wherein;
the expected healthcare experience data for each of the two or more healthcare benefit plans comprises data indicating specific healthcare providers available.

9. The computer program product for providing a process for healthcare benefit plan selection of claim 1, wherein;
the expected healthcare experience data for each of the two or more healthcare benefit plans comprises data indicating specific healthcare services available.

10. A computer program product for providing a process for healthcare benefit plan selection comprising:
a nontransitory computer readable medium;
and computer program code, encoded on the computer readable medium, comprising computer readable instructions for:
defining a timeframe;
obtaining actual general/demographic data of a healthcare consumer;
obtaining actual historical healthcare service utilization data of the healthcare consumer;
obtaining actual personal health profile data of the healthcare consumer wherein the personal health profile data associated with the healthcare consumer comprises data indicating one or more of the healthcare consumer's activities;
analyzing the actual general/demographic data, the actual historical healthcare service utilization data, and the actual personal health profile data of the healthcare consumer to create predicted healthcare services utilization data, the predicted healthcare services utilization data comprising specific healthcare services the healthcare consumer is likely to utilize during the defined timeframe wherein the predicted healthcare services utilization data is at least partly derived through the analysis of the healthcare consumer's activities, wherein the process is further configured to consider whether the healthcare consumer is likely to benefit from or suffer from illnesses or conditions resulting from athletic activities indicated in the personal health profile data;
obtaining data associated with the rules governing the operation and of use of two or more healthcare benefit plans;
determining the expected healthcare consumer's cost for the healthcare services the healthcare consumer is predicted to utilize during the defined timeframe using the predicted healthcare services utilization data and the data associated with the rules governing the operation and of use of two or more healthcare benefit plans;
comparing the expected healthcare consumer's cost for the healthcare services the healthcare consumer is predicted to utilize during the defined timeframe for each of the two or more healthcare benefit plans to create expected healthcare consumer's cost comparison data; and
providing the expected healthcare consumer's cost comparison data to the healthcare consumer.

11. A system for providing healthcare benefit plan selection comprising:
a processor;
a memory coupled to the processor, the memory having processor executable instructions stored therein, the processor executable instructions when executed perform a process for healthcare benefit plan selection, the process for healthcare benefit plan selection comprising:
defining a timeframe;
obtaining actual general/demographic data of a healthcare consumer;
obtaining actual historical healthcare service utilization data of the healthcare consumer;
obtaining actual personal health profile data of the healthcare consumer wherein the personal health profile data associated with the healthcare consumer comprises data indicating one or more of the healthcare consumer's activities;
analyzing the actual general/demographic data, the actual historical healthcare service utilization data, and the actual personal health profile data of the healthcare consumer to create predicted healthcare services utilization data, the predicted healthcare services utilization data comprising specific healthcare services the healthcare consumer is likely to utilize during the defined timeframe wherein the predicted healthcare services utilization data is at least partly derived through the analysis of the healthcare consumer's activities, wherein the process is further configured to consider whether the healthcare consumer is likely to benefit from or suffer from illnesses or conditions resulting from athletic activities indicated in the personal health profile data;

obtaining data associated with the rules governing the operation and of use of two or more healthcare benefit plans;

creating expected healthcare experience data for each of the two or more healthcare benefit plans using the predicted healthcare services utilization data and the data associated with the rules governing the operation and of use of two or more healthcare benefit plans;

comparing the expected healthcare experience data for each of the two or more healthcare benefit plans; and providing selection data to the healthcare consumer, the selection data being based, at least in part, on the comparison of the expected healthcare experience data for each of the two or more healthcare benefit plans, the selection data being used by the healthcare consumer to assist the healthcare consumer in selecting at least one of the two or more healthcare benefit plans.

12. The system for providing healthcare benefit plan selection of claim 11, wherein;

the selection data comprises a recommendation as to which one or more of the two or more healthcare benefit plans the healthcare consumer should select.

13. The system for providing healthcare benefit plan selection of claim 11, wherein;

the selection data comprises data representing the comparison of the expected healthcare experience data for each of the two or more healthcare benefit plans.

14. The system for providing healthcare benefit plan selection of claim 11, wherein;

the historical healthcare service utilization data associated with the healthcare consumer comprises data indicating the healthcare consumer's inclination to utilize preventative/maintenance healthcare services, further wherein;

the predicted healthcare services utilization data is based, at least in part, on the data indicating the healthcare consumer's inclination to utilize preventative/maintenance healthcare services.

15. The system for providing healthcare benefit plan selection of claim 11, wherein;

the personal health profile data associated with the healthcare consumer comprises data indicating the healthcare consumer's pre-disposition to injury and/or disease based on the healthcare consumer's historical attitude toward healthcare services utilization, further wherein;

the predicted healthcare services utilization data is based, at least in part, on the healthcare consumer's historical attitude toward healthcare services utilization.

16. The system for providing healthcare benefit plan selection of claim 11, wherein;

the personal health profile data associated with the healthcare consumer comprises data indicating the healthcare consumer's pre-disposition to injury and/or disease based on the healthcare consumer's family history, further wherein;

the predicted healthcare services utilization data is based, at least in part, on the healthcare consumer's family history.

17. The system for providing healthcare benefit plan selection of claim 11, wherein;

the expected healthcare experience data for each of the two or more healthcare benefit plans comprises expected healthcare consumer out-of-pocket costs.

18. The system for providing healthcare benefit plan selection of claim 11, wherein;

the expected healthcare experience data for each of the two or more healthcare benefit plans comprises data indicating specific healthcare providers available.

19. The system for providing healthcare benefit plan selection of claim 11, wherein;

the expected healthcare experience data for each of the two or more healthcare benefit plans comprises data indicating specific healthcare services available.

* * * * *